(12) United States Patent
Price et al.

(10) Patent No.: US 7,674,603 B2
(45) Date of Patent: Mar. 9, 2010

(54) MICROORGANISM DETECTOR

(75) Inventors: Robert Graham Price, Northwood (GB); Nicola Karen Browne, Wye (GB)

(73) Assignee: Prail Price Richardson Diagnostics Limited, London (GB)

( * ) Notice: Subject to any disclaimer, the term of this patent is extended or adjusted under 35 U.S.C. 154(b) by 154 days.

(21) Appl. No.: 10/583,050

(22) PCT Filed: Dec. 21, 2004

(86) PCT No.: PCT/GB2004/005348

§ 371 (c)(1),
(2), (4) Date: Nov. 3, 2006

(87) PCT Pub. No.: WO2005/061723

PCT Pub. Date: Jul. 7, 2005

(65) Prior Publication Data

US 2007/0117172 A1 May 24, 2007

(30) Foreign Application Priority Data

Dec. 22, 2003 (GB) .................................. 0329697.7

(51) Int. Cl.
*C12Q 1/04* (2006.01)

(52) U.S. Cl. .......................................... 435/34; 424/56
(58) Field of Classification Search .................. 435/34, 435/56

See application file for complete search history.

(56) References Cited

U.S. PATENT DOCUMENTS

| 5,096,668 | A | * | 3/1992 | Thompson | .................... | 422/58 |
| 5,221,606 | A | * | 6/1993 | Richardson et al. | ............ | 435/4 |
| 5,464,755 | A | * | 11/1995 | Bochner | ...................... | 435/34 |

FOREIGN PATENT DOCUMENTS

| JP | 2001 321196 | * | 11/2002 |
| WO | WO 02/33414 | * | 4/2002 |

* cited by examiner

*Primary Examiner*—Ralph Gitomer
(74) *Attorney, Agent, or Firm*—Kilpatrick Stockton LLP (57) ABSTRACT

The invention relates to devices and methods for detecting and identifying microorganisms comprising a porous body having regions of differing pore size, said regions being associated with different chromogens specific to enzymes produced by microorganisms. Devices and methods according to the present invention may be useful in the detection and identification of food and water borne microorganisms as well as in the detection of bacteria that may be associated with infection, such as urinary tract infection.

20 Claims, 4 Drawing Sheets

Fig 1: *A Typical Lateral Flow Dipstick.*

Fig 2: *A typical Flow Through Dipstick.*

After colour development

Figure 6c

MICROORGANISM DETECTOR

TECHNICAL FIELD

The present invention discloses a method for the rapid detection of bacteria particularly in body fluids, but also in other applications such as water purification and in the food preparation industry; and also to devices to undertake detection of bacteria.

BACKGROUND ART

Almost 5 million women suffer from a urinary tract infection (UTI) each year. Urinary tract infection affects about 20% of women annually, and approximately 50% of women suffer from at least one bout of UTI in their lifetime, contributing significantly to hospital laboratory workloads. Following an ESCMID study carried out in 2001, it was shown that only 19% of hospitals within the EU carry out standard screening procedures as the norm. Asymptomatic bacteraemia in catheter patients are largely responsible for the increase in the number of antibiotic resistant organisms found in the hospital setting.

UTI is predominantly caused by a small range of organisms: *Escherichia coli, Staphylococci, Proteus mirabilis, Enterococci, Kiebsiella; Bacillus* (Gruenberg, 1980) and *Candida albicans* have also been implicated in UTI (Voss et al., 1994). *Escherichia coli* is the most common, however *Candida* infections are of particular concern as the organism is capable of ascending the urinary tract and it may lead to disseminated disease including renal disease. It is generally recognised that more than $10^5$ bacteria/ml are needed to confirm the presence of urinary tract infection whereas values below $10^3$ bacteria/ml are largely due to cross contamination. The development of a rapid method for detecting UTI, and identifying the causative organism is of primary importance, however, the availability of a generic method allowing improved detection of specific types of bacteria in body fluids would have wider medical significance. For example, the detection of bacteraemia (bacteria in blood) is of critical importance. There are additionally many non-clinical situations in which rapid differential diagnosis of microorganisms would be of significance, including detection of faecal indicator bacteria.

The role of a universal detection system for UTI organisms has already been demonstrated and a commercial kit based on nitrate detection is marketed in the USA. However this test is based upon a metabolic activity that is not present in all UTI organisms, for example *Enterococcus* spp. and therefore could give false negative results. Other limitations of this test are that false negative results may be produced through a lack of nitrates in a vegetarian diet or excess intake of ascorbic acid (Vitamin C). Urine also needs to be retained for 4-6 hours prior to the test. When trying to control a UTI infection the patient is advised to drink increased quantities of fluid thus posing a problem for urine retention.

When testing for the presence of a microorganism, it is common practice in microbiology to incorporate a hydrolytic chromogenic substrate into the growth medium, so that any organism expressing the appropriate enzyme for this substrate will hydrolyse it thereby releasing the coloured chromogen and acting as an indicator for the presence of a microorganism. This has commonly been carried out with X-D-galactosides and X-D-glucuronides, which detect coliforms and *E. coli*, respectively.

U.S. Pat. No. 5,221,606 discloses the use of chromogenic phenols, which have solubilising groups attached to them, such as carboxyl and quaternary ammonium groups, or both, which impart a certain degree of water solubility to their derived carboxylic ester derivatives.

Merely making a soluble chromogenic substrate is not enough however. It is important that the colour released on action of the enzyme remains localised with the bacterial colony that produced the enzyme, otherwise identification of bacteria would be difficult. Ideally a test would provide a chromogenic substrate which would impart a characteristic colour to different bacterial colonies.

We have demonstrated the selective absorption of chromophoric phenols (released from chromogenic substrates by microbial enzymatic activity) onto membranes in U.S. Pat. No. 5,221,606. It has been shown that several of the chromophores are tightly bound to types of membrane. Also, on binding, the intensity of the colour increases and may change (e.g. from red to blue), depending on the particular chromophore released.

By incorporating a rapid and cheap method of screening to replace the lengthy procedures currently being used, the accurate detection of a UTI and determination of the causative organism would enable appropriate antibiotic treatment to be given to patients at an early stage.

Figure 1:
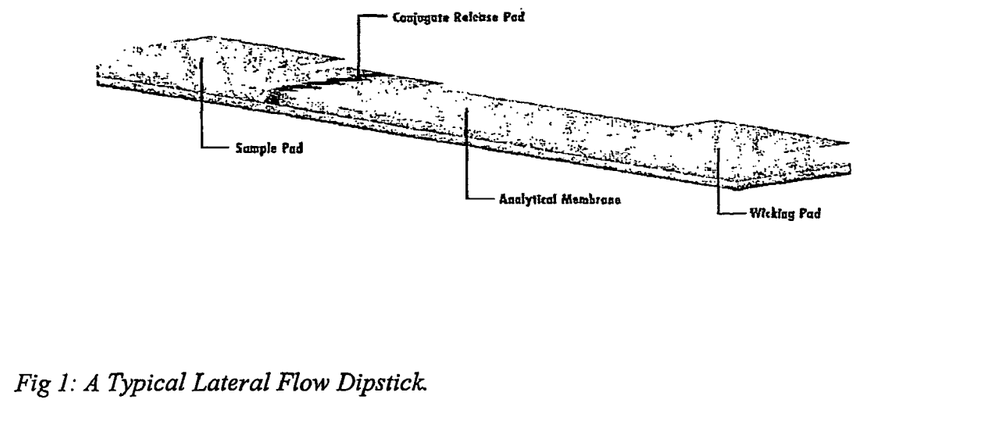
FIG. 1 shows a typical lateral flow dipstick as known in the art

A common device for identifying substrates in body fluid is a dip-stick. There are two dip-stick formats used in a number of products on the market today. The most commonly used format is the lateral flow e.g. the pregnancy test. A typical lateral flow involves four main sections: sample application pad, conjugate release pad, analytical membrane and the wick (FIG. 1). Each section will have different characteristics such as absorption, wicking rates and binding properties thereby allowing a good flow through and clear results. The lateral flow format is generally used in the detection of compounds by antibodies and its main advantages are ease of use and speed.

Figure 2:
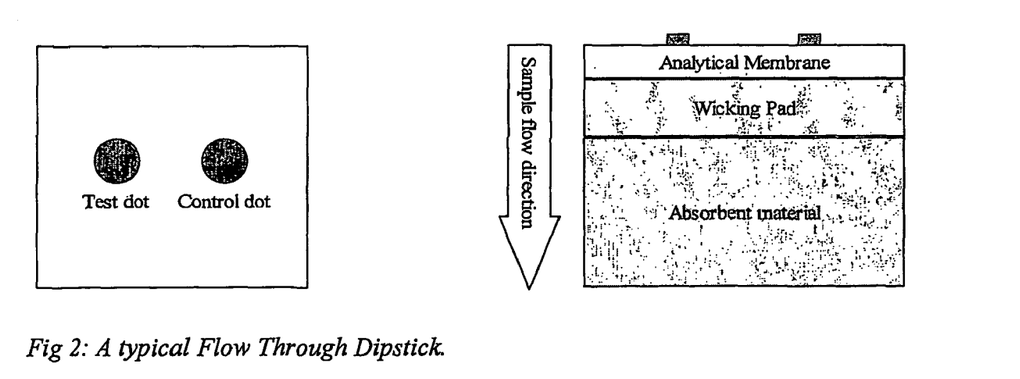
FIG. 2 shows a typical flow though dipstick as known in the art

The second format is the flow through which acts to concentrate the sample (FIG. 2). Greater volumes of fluid can be added to the test. The main disadvantage of the flow though is that in the majority of cases, especially those involving antibodies, a multi-step washing process needs to be carried out, thereby making it unsuitable for home testing.

The applicants have discovered that an improvement to the effectiveness of detection devices can be made by adding filtration means to the devices to separate differently sized microorganisms. Microorganisms can then be directed to discrete areas where they react with particular chromogens.

DISCLOSURE OF THE INVENTION

The present invention is a device for the characterisation of microorganisms comprising a porous body having regions of differing pore size said regions being associated with different chromogens specific to enzymes produced by microorganisms.

BRIEF DESCRIPTION OF THE DRAWINGS

The invention is illustrated in the following description with reference to the figures.

DETAILED DESCRIPTION OF THE INVENTION

In preparing devices of the present invention, substrates have been utilised in a rapid test for urinary tract infection (UTI). Substrates have been selected on the basis of their ability to detect specific organisms. The enzyme activities include phosphatases, esterases, N-acetyl-β-glucosaminidase, galactosidases and glucosidases. For example esterase activity is detectable in a range of bacteria using the chromogenic substrate (SLPA butyrate [(E)-3-4-(butyryloxy)-3,5-dimethoxystyryl)quinolinium-1-yl)propanoate, ammonium salt]), PPR Diagnostics Ltd), which gives a bright purple colour on hydrolysis. (Miles et al., 1992, Cooke and Richardson 1999).

The following chromogenic substrates were selected on the basis of their specificity, their ability to produce a coloured end product, and availability:

1) Indoxyl butyrate (IB)—hydrolysed by esterases.
2) Indoxyl glucoside (IG)—hydrolysed by the enzyme glucosidase.
3) Esculin—hydrolysed to esculetin and dextrose. Esculetin then reacts with ferric ammonium citrate to form a brown-black product.
4) Magenta glucoside—hydrolysed by β-galactopyranoside.
5) Red-β-glucuronide—hydrolysed by β-glucuronide.
6) 2-methoxy-4-(2-nitrovinyl) phenyl β-D-glucopyranoside (MNP-glc)—hydrolysed by glucosidase.
7) 2-methoxy-4-(2-nitrovinyl)phenyl β-D-2-acetamindo-2-deoxyglucopyranoside (MNP-glcNAc)—hydrolysed by glucosaminidase.
8) 5-Bromo-4-Chloro-3-Indoxyl-beta-D-Glucuronide, Cyclohexylammonium Salt (X-Glc)—hydrolysed by glucuronidase found only in E. coli.
9) 5-Bromo-4-Chloro-3-indoyl-beta-D-Galactopyranoside (X-gal)—hydrolysed by galactosidase found only in E. coli.

Some substrates are highly susceptible to fluctuations in pH, therefore it was important to assess whether this was the case with these substrates. The pH proved not to be a problem as demonstrated by tests carried out on IB (table 1). The blue colour produced as a direct result of hydrolysis only developed in the presence of both the esterase enzyme and an alkaline pH, and remains clear when pH 9.90 is added alone.

TABLE 1 indicates that Indoxyl butyrate is not susceptible to non-enzymatic hydrolysis by alkaline pH's.

| Added to the Indoxyl butyrate solution. | Colour development after 5 min | Colour development after 15 min | Colour development after 30 min |
|---|---|---|---|
| Esterase enzyme | Clear | Clear | Clear |
| Esterase enzyme and pH 9.90 | Very light blue | Light blue | Blue |
| pH 9.90 | Clear | Clear | Clear |
| Control (no additions) | Clear | Clear | Clear |

Following further testing, additional problems of substrate stability both on and off the membrane became apparent with four of the substrates. Both MNP-glc and MNP-glcNAc substrates which produced a red colour on hydrolysis, were subject to rapid fading of colour after 2 hours. In the case of Red-β-glucuronide, the substrate failed to give any colour indication two weeks after initial tests were carried out indicating poor solid substrate stability.

Experimentation into the correct concentrations that were required to achieve clear colour production for each substrate was carried out. These figures have been tabulated below along with substrate preparation, colour production on hydrolysis and the corresponding reacting organisms (table 2).

TABLE 2

Overview of substrates and the organisms that hydrolyse them.
Indoxyl glucoside was omitted from the test as it was playing an identical role to that of Esculin. This therefore meant that any bright turquoise colour produced was purely the result of E. coli.

| Organism | Substrates and the organisms that cause their enzymatic hydrolysis | | | | | |
|---|---|---|---|---|---|---|
| | Indoxyl butyrate Greyhound | Indoxyl Glucoside Glycosynth | Esculin Sigma | Magenta-glucoside Inalco | X-glc Inalco | X-gal Inalco |
| Concentrations (100 ml water) | 0.04 g | 0.06 g | 0.1 g + 0.05 Ferric ammonium citrate | 0.02 g | 0.04 g | 0.02 g |
| E. coli | Blue | | | | Bright turquoise | Bright turquoise |
| B. subtilis | Blue | Bright turquoise | Black | Pale pink | | |
| P. mirabilis | Blue | | | | | |
| E. faecalis | Blue | Bright turquoise | Black | Purple | | |
| Klebsiella | Blue | | Black | Pink | | Pale blue |
| Pseudomonas | Blue | Bright turquoise | Black | Purple | | |
| Candida | Blue | | | | | |

Having established that esculin, Magenta-G and X-gal and X-glc were feasible for the rapid test, the most appropriate solid matrix was needed. Membranes from three major companies, Whatman, Pall and Schleicher & Schuell, were assessed and compared. Those membranes with high absorptive properties resulting in clear colour production were needed. In addition, to prevent fading of colour, they would have to retain the released chromophore.

Following several repeat experiments to assess the 'best' membrane it became evident that the key component of the membranes that promoted colour development was cellulose. Cellulose membranes were seen to allow greater colour development and were not prone to fading. The 12S membrane from the Schleicher and Schuell range, a 90% cellulose and 10% rayon membrane, was chosen from the final selection to be incorporated in the dip stick.

The sensitivity of the test is also highly important. With a UTI, it is not the presence of bacteria that is the defining factor, but the level at which they are present. Therefore we must have a test that is able to detect different bacteria, but only from a certain number and upwards i.e. within the region of >$10^4$ bacteria/ml to avoid false positives. Initial substrate testing was carried out using concentrated liquid cultures of the panel organisms, and therefore the next stage was to test dilution of the liquid cultures using a serial dilution from $10^{-1}$ to $10^{-6}$. These dilutions were tested out on 12S membranes previously soaked in substrate solutions and left to incubate at 37° C. The times recorded for colour levels to reach a certain intensity were seen to increase at a graduated rate as the level of infection fell e.g. in the detection of *B. subtilis* using Esculin, an infection in the region of $10^{-6}$ bacterial/ml would be detected with ½ hr where as a borderline case ($10^4$ bacteria/ml), would take up to 3 hrs.

In order to speed up reaction times magnesium was added, and identical experiments were carried out incorporating a solution of 0.1M $MgCl_2$ to assess whether or not colour production by the substrates improved. 12S membranes were soaked individually in a solution of the substrate and $MgCl_2$ for 3 hours, dried at 37° C. and cut into 2 cm×0.5 cm strips to which samples of the panel organisms were added (table 3).

tification of an infection from a high level i.e. >$10^5$ bacteria/ml infection to a possible borderline case would take from 1 to 3 hours.

β-galactoside substrate is often used in the identification of *E. coli* strains on agar plates, where a blue colour indicates the enzymes presence. In addition, by incorporating IPTG in the agar, colour production is greatly enhanced.

To test if addition of IPTG was a possible method to increase colour production on the 12S membranes, 0.5 ml of 100 mM IPTG was added to 50 ml of distilled water containing 0.02 g X-gal and used to soak 12S membranes. There was a slight improvement in the intensity of the colour production, which following the initial tests was further improved by doubling the quantity of 100 mM IPTG used. This experiment further confirmed that the substrate was specific to *E. coli* and was able to detect the bacteria present at sensitive levels without producing any false positives (table 4). Further improvements in the detection of *E. coli* were made by combining both the β-galactoside substrate with the glucoside to give a clear, bright turquoise colour on the 12S membrane following hydrolysis.

TABLE 4

Detection times for *E. coli* using X-gal substrate with IPTG.

| *E. coli* concentration levels in urine Serial dilution | OXOID - PO0794 Chromogenic results | UTI Levels | Confirmed Detection Results |
|---|---|---|---|
| $10^{-1}$ | Uncountable no. of colonies | Definite UTI +++ | Infection detected in 1 hr, and confirmed in 2 hrs |
| $10^{-2}$ | 60 colonies | UTI ++ | Infection detected in 2 hrs and confirmed in 4 hrs |
| $10^{-3}$ | 11 colonies | No UTI | Colour was seen >4 hrs |
| $10^{-4}$ | 0 colonies | No UTI | No infection |

TABLE 3

Comparison of reaction times to give a positive colour with and without $MgCl_2$ for each of the panel organisms.

| | Esculin | | Magenta-glucoside | | X-galactoside | | Glucuronide | |
|---|---|---|---|---|---|---|---|---|
| Organisms | Substrate only | +$MgCl_2$ | Substrate only | +$MgCl_2$ | Substrate only | +$MgCl_2$ | Substrate only | +$MgCl_2$ |
| *E. coli* | N/A | N/A | N/A | N/A | 2 hr | 1½ hr | 2 hrs | 1 hr |
| *B. subtilis* | 1 hr | 40 min | No colour | 3 hrs | N/A | N/A | N/A | N/A |
| *E. faecalis* | 2 hr | 1½ hrs | 2 hrs | 2 hrs | N/A | N/A | N/A | N/A |
| *Pseudomonas* | 2 hrs | 1 hr 40 min | 3 hrs | 2 hrs | N/A | N/A | N/A | N/A |
| *Klebsiella* | 2½ hrs | 2½ hrs | N/A | N/A | N/A | N/A | N/A | N/A |

The results indicate that the $Mg^{2+}$ ions do enhance the reaction times, especially when there are a lower number of the organisms present, therefore increasing the test sensitivity. *B. subtilis* also appears to be reacting with the Magenta-g substrate as a pale pink colour developed after 3 hours incubation. This was not evident in previous experiments, and is most likely the result of the $MgCl_2$. The pale pink colour produced compared to that of the deep pink/purple colour seen in the case of *E. faecalis*, may still be sufficient in order to differentiate between the two organisms. Overall the iden- TABLE 4-continued Detection times for *E. coli* using X-gal substrate with IPTG.

| *E. coli* concentration levels in urine Serial dilution | OXOID - PO0794 Chromogenic results | UTI Levels | Confirmed Detection Results |
|---|---|---|---|
| $10^{-5}$ | 3 colonies | No UTI | No infection |
| $10^{-6}$ | 0 colonies | No UTI | No infection |
| $10^{-7}$ | 0 colonies | No UTI | No infection |

TABLE 4-continued

Detection times for E. coli using X-gal substrate with IPTG.

| E. coli concentration levels in urine Serial dilution | OXOID - PO0794 Chromogenic results | UTI Levels | Confirmed Detection Results |
|---|---|---|---|
| Control urine sample | 0 colonies | No UTI | No infection |
| Autoclaved urine sample | 0 colonies | No UTI | No infection |

Urine contains a number of constituents which will vary in amounts from individual to individual. In addition, chemical balances such as the pH level have the potential to affect the substrates causing possible non-enzymatic hydrolysis and false positive results. Therefore it was essential to test the substrate under such harsh conditions. Liquid cultures of individual organisms were used to spike urine samples and left to incubate at 37° C. for 2½ hours (average urine retention time in the bladder) prior to analysis. OXOID chromogenic media CM949 identifies *E. coli*, *E. faecalis* and *B. subtilis* infections in urine following 24 hour incubation on the agar. Spiked urine samples were also tested with this media using MAST Bacteruritest strips (product reference BTR1), the formation of 20 colonies or more would confirm a UTI infection. Testing of the rapid membrane system was run along side this standard method used in laboratories today to validate whether there was an infection at numbers $>10^4$ Bacteria/ml in the spiked urine samples.

It was important to assess the sensitivity of the substrates in this new environment. Therefore urine samples were spiked with three bacteria concentration levels and following 2½ hrs incubation at 37° C., samples were applied to the 12S membranes previously soaked in the various substrates (table 5). The only substrate that was affected by the urine was IB, which was seen to give false positives. Naturally occurring urine esterases were later found to be the cause, resulting in the substrate being 'omitted' from the test. Detection levels have remained within the region of 1 hour to 3 hours depending on the level of infection.

ment pad. However it was necessary to identify the most suitable membranes for the sample application pad (SAP) and the wick, as these effect both sample volume added and flow through.

The function of the sample application pad is not only to act as a pre-filter, but also to stabilise the sample with respect to pH and salt conditions. The pH of urine is known to vary from pH 5-11, and therefore in order to ensure that the enzymes are able to hydrolyse the substrates within reasonable time limits, and that the substrates are not broken down non-enzymatically as a result of conditions which are too acidic or alkaline, the sample application pad is soaked in a phosphate buffer. A number of membranes were tested for use as the sample application pad, all of which had a hydrophobic matrix with no affinity or a negative affinity to the sample. Of the membranes we tested, the 903 membrane from the Schleicher and Schuell range was selected due to the rapid absorption of the sample thereby allowing a reasonable volume to be added, and good even colour production.

The wick has similar quality requirements to that of the sample application pad in that it must have good absorption properties to prevent the backflow of the sample and to act as a sink, drawing the liquid down the entire length of the strip. However it must not drag the colour down to the base of the strip as this would effect the reading of the sample. This was found to be the case when the more absorptive membranes were tested. Following several tests, the 903 membrane was again selected to act as the wick.

We also had to consider three additional factors when designing the UTI dipstick format:
1) The feasibility of incorporating several substrates on to one membrane.
2) Separation of the individual organisms based on physical parameters therefore allowing specific identification.
3) Concentration of the sample.

Experiments to discern whether it was possible to incorporate more than one substrate on to the membrane, and that it would react with the correct organism proved to be successful. There was no decrease in colour production and in the case where one organism reacted with both substrates, a hybrid colour of the two was clearly evident.

At this stage it was important to separate the organisms as *B. subtilis*, *E. faecalis* and *Pseudomonas* were reacting with

TABLE 5

Detection Times for three of the Panel Organisms in Spiked Urine.

| Organism | Conc. levels in urine | OXOID Chromogenic substrate results | UTI Levels | Confirmed Detection Results |
|---|---|---|---|---|
| E. coli | $10^{-1}$ | Uncountable no. of colonies | Definite UTI +++ | Definite *E. coli* detection in 2-3 hrs |
|  | $10^{-2}$ | Uncountable no. of colonies | Definite UTI +++ | Definite *E. coli* detection in 2-3 hrs |
|  | $10^{-3}$ | 50 colonies | UTI ++ | Definite *E. coli* detection in 3-4 hrs |
| B. subtilis | $10^{-1}$ | Uncountable no. of colonies | Definite UTI +++ | Definite infection detection in 1 hr |
|  | $10^{-2}$ | Uncountable no. of colonies | Definite UTI +++ | Definite infection detection in 1-2 hrs |
|  | $10^{-3}$ | Uncountable no. of colonies | Definite UTI +++ | Definite infection detection in 2-3 hrs |
| E. faecalis | $10^{-1}$ | Uncountable no. of colonies | Definite UTI +++ | Definite infection detection in 1 hr |
|  | $10^{-2}$ | 60 colonies | UTI ++ | Definite infection detection in 1 hr |
|  | $10^{-3}$ | 10 colonies | No UTI | Colour seen after 4 hrs. |
| Control urine sample | N/A | No colonies | No UTI | No infection |
| Autoclaved urine sample | N/A | No colonies | No UTI | No infection |

We have established that a 12S membrane is the most suitable for the 'analytical membrane' or the colour developthe same combination of substrates. This made them detectable, but detection was not specific to the individual organisms. However their physical properties such as size and charge can be used to separate out the organisms, and therefore by combining a step-by step filtration system into the dipstick we were able to see reactions on different membranes which would be specific to that individual organism.

There are a wide range of membrane pore sizes available. For the purposes of separation of the different organisms, we required membranes whose pore sizes fell within a range of 0.3 μm to 4.0 μm. Membranes from the Schleicher & Schuell range and Whatman range were selected on the basis of these characteristics.

ME26 with pore size of 0.6 μm
GF/F with pore size of 0.7 μm
ME27 with pore size of 0.8 μm
GF/B with pore size of 1.0 μm
ME28 with pore size of 1.2 μm
GF/AVA with pore size of 1.7 μm
ME29 with pore size of 3.0 μm
G/DVA with pore size of 3.51 μm Filtration experiments were then carried out in order to assess their capabilities in separating the organisms. ME26 did not allow any of the organisms through as the pores were too small. ME27 allows colonies of *E. coli, B. subtilis* and *Klebsiella* to pass through, separating out *Pseudomonas* and *E. faecalis*. In contrast ME29 allows all organisms to pass through.

Filtration of organisms though the membranes was seen as follows:

The third objective which is concerned with the concentration of the sample was then solved by incorporating several layers, into the dipstick. This approach aids in concentrating the bacteria as the liquid is dragged through to the base.

Figure 3:
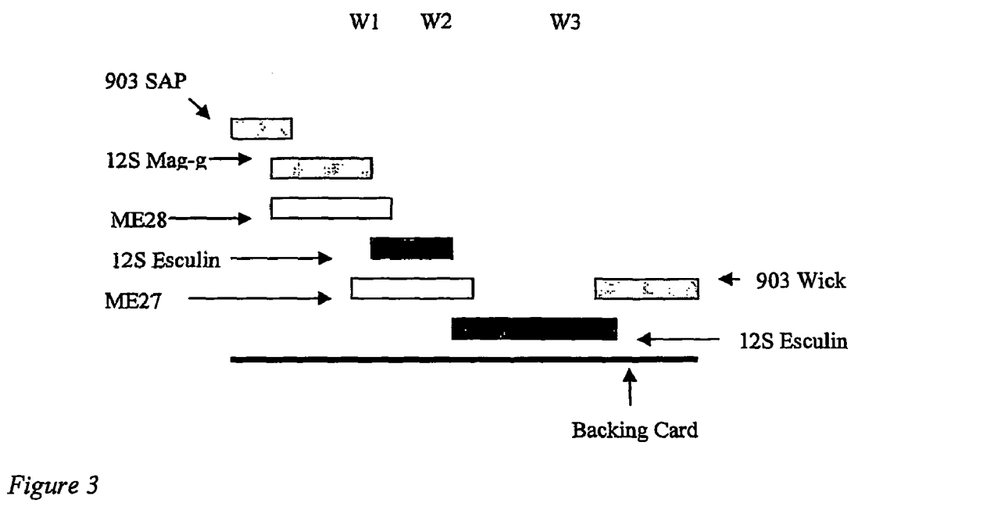
FIG. 3 shows a layered device in accordance with the invention

Therefore having taken all these factors into consideration, the dip-stick prototype was produced (FIG. 3). Windows 1, 2 and 3 refer to the colour development pads which when viewed from the top will give a reading. By applying approximately 0.5 ml of a sample on to the sample application pad, and periodically checking the dipstick for colour development in the windows white at 37° C., the patients outcome can be assessed.

Through out the trial runs of various dipstick prototypes, a number of additional considerations that needed to be taken into account came to light. One of the major problems was the substrate concentration on the membranes and their order on the dipstick. Following the first round of experiments, colour from one membrane was seen to migrate to the adjoining ones, combining the colours and therefore preventing a clear reading from being taken. By experimenting with the substrate order and concentration (table 7) as well as the level to

TABLE 6

Filtration of organisms though membranes

|  | ME26 | GF/F | ME27 | GF/B | ME28 | GF/AVA | ME29 | G/DVA |
|---|---|---|---|---|---|---|---|---|
| *E. Coli* | x | ✓ | ✓ | ✓ | ✓ | ✓ | ✓ | ✓ |
| *Klebsiella* | x | x | ✓ | ✓ | ✓ | ✓ | ✓ | ✓ |
| *B. Subtilis* | x | x | ✓ | ✓ | ✓ | ✓ | ✓ | ✓ |
| *Pseudomonas* | x | x | x | x | ✓ | ✓ | ✓ | ✓ |
| *E. Faecalis* | x | x | x | x | x | ✓ | ✓ | ✓ | which the adjoining membranes overlapped a solution was provided for this problem.

TABLE 7

A comparison of three different dipstick formats. Bold writing indicates false results.

| Organism | Conc. Levels in Urine - serial dilution | OXOID Chromogenic | UTI Levels | Assessment of Format 1 | Assessment of Format 2 | Assessment of Format 3 |
|---|---|---|---|---|---|---|
| *E. coli* | $10^{-1}$ | Deep pink +++ | High level UTI | *E. coli* detected in 1 hr | *E. coli* detected in ½ hr | *E. coli* detected in 1½ hr |
|  | $10^{-3}$ | 40 colonies | UTI | *E. coli* detected in 1 hr | *E. coli* detected in 3 hrs | *E. coli* detected in 3 hrs |
|  | $10^{-5}$ | 10 colonies | No infection | E.coli detected in 1 hr. | No infection | No infection |
| *B. subtilis* | $10^{-1}$ | Dark green +++ | High level UTI | No infection | Pink in 3 hrs | Pink and brown in 3 hrs |
|  | $10^{-3}$ | 30 colonies | UTI | No infection | Blue in 3 hrs | Pink and brown in 3 hrs |
|  | $10^{-5}$ | 5 colonies | No infection | No infection | Blue in 4 hrs | No infection |
| *E. faecalis* | $10^{-1}$ | Light blue ++ | High level UTI | Brown in 1 hr | Pink and brown in 2 hrs | Pink and brown in 1 hr |
|  | $10^{-3}$ | 25 colonies | UTI | Blue in 3 hrs | Blue in 2 hrs, pink in 3 hrs | Pink and brown in 3 hrs |
|  | $10^{-5}$ | 2 light blue and 3 pink *E. coli* colonies | No infection | Blue in 3 hrs | Blue and pink in 3 hrs | Blue in 3 hrs. |

TABLE 7-continued

A comparison of three different dipstick formats. Bold writing indicates false results.

| Organism | Conc. Levels in Urine - serial dilution | OXOID Chromogenic | UTI Levels | Assessment of Format 1 | Assessment of Format 2 | Assessment of Format 3 |
|---|---|---|---|---|---|---|
| Pseudomonas | $10^{-1}$ | Light blue +++ | High level UTI | Brown in 1 hr | Pink and brown in 1½ hr | Pink and brown in 1½ hr |
|  | $10^{-3}$ | 20 colonies | Borderline case | Blue in 1 hr | Blue in 3 hrs | Pink and brown in 4 hrs |
|  | $10^{-5}$ | 1 colony | No infection | No infection | No infection | No infection |
| Mixed Urine Sample | $10^{-1}$ | Mix of deep pink and dark green +++ | High level UTI | E. coli detection in 1½ hrs | E. coli detection in 1 hr and pink in 2 hrs. | E. coli detection in ½ hr and pink in 1½ hr |
|  | $10^{-3}$ | 15 E. coli and 20 B. subtilis colonies | UTI | No infection | E. coli in 1 hr and pink in 3 hrs | E. coli 3 hrs and pink in 3 hrs |
|  | $10^{-5}$ | 6 E. coli and 10 B. subtilis colonies. | Borderline infection | No infection | No infection | Pink in 3 hrs. |
| Control Urine Sample | N/A | No infection | No infection | No infection | No infection | No infection |
| Autoclaved Urine Sample | N/A | No infection | No infection | No infection | No infection | No infection |

Format 1 (W1 = IB, W2 = Mag-g + X-gal + glc, W3 = Esculin (0.04 g/50 ml))
Format 2 (W1 = IB, W2 = Mag-g, W3 = Esculin (0.04 g/50 ml) + X-gal + glc)
Format 3 (W1 = Mag-g W2 = X-gal + glc W3 = Esculin (0.05 g/50 ml))

Figure 4:
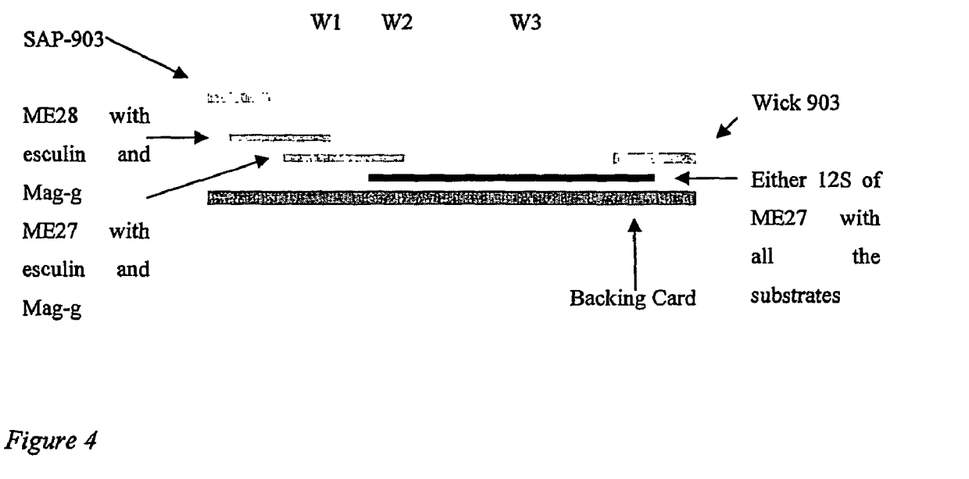
FIG. 4 shows a specific layered device in accordance with the invention

It was found that by placing the X-gal and Glc at position W3, the bright blue colour produced on hydrolysis was maintained in this window. If the sample contained organisms that reacted with both Esculin and X-gal+Glc, then the colours were strong enough for both to come through. Secondly, the end format involving the separation of the organisms using the ME membranes effected the substrates final combinations, the format as shown in FIG. 4 having 3 windows and using the reagents Magenta-g, X-gal+glc and Esculin was selected. A number of possible readings can be seen and have been shown below in order to indicate how they would be interpreted (table 8). Window 1 shows the results of ME28 with esculin and Mag-g membrane, window 2 shows the results of ME27 with esculin and Mag-g membrane, window 3 shows the results of 12S or ME27 with esculin, Mag-g and X-gal and X-glc membrane subject to filtration though ME27 membrane.

TABLE 8

Examples of possible infections and their interpretations.

| Results | UTI infection | Reasons |
|---|---|---|
| W3 = blue | E. coli | Only E. coli reacts with X-gal and glc to produce a blue colour. |
| W1 = brown W2 = brown W3 = brown + blue | E. coli and B. subtilis | Same as above and B. subtilis is able to pass through all the filters and only produces a strong colour with Esculin |
| W1 = brown + purple W2 = brown W3 = brown | B. subtilis and E. feacalis | Same reason as above for B. subtilis. E. faecalis reacts with both Esculin and Mag-g strongly, however is unable to pass through the ME28 membrane. |
| W1 = pink + brown W2 = pink + brown W3 = brown | B. subtilis, Pseudomonas and possibly E. feacalis | Same reasons as above for B. subtilis. Definitely Pseudomonas present as able to pass through ME28. E. faecalis could be involved, but unlikely to have such a multiple level infection. |

W1 = window 1, W2 = window 2, W3 = window 3

In order to design a successful dipstick it was necessary to consider the substrate order (individually soaked membranes and/or combinations) and type, the use of separate filters or combined filters and their properties, the length of overlap between membranes to avoid colour overlap, the membrane type used for the analytical membrane, the sample application pad and type of membrane used and size, and the type of membrane used for the wick and its size.

Manufacturing factors which were considered included, length of time to soak membrane in substrate solutions, length of membrane drying time at 37° C. and conditions, substrate concentrations used and storage conditions of membranes i.e. shelf life.

Panel Test

The panel test as viewed from above and is seen as a series of rows comprising of individual squares. Each row corresponds to a substrate, and each column to the filtration capacity. The filter is placed over the membrane containing the chromophores. When testing out a sample of urine, approximately 0.5 ml of urine should be applied to the centre of each square slowly to prevent maximum downward absorption. Liquid then filters though the pore sized membranes and organisms selectively contact the substrate depending on the degree of filtration. The panel test should then be placed on a flat surface in a well ventilated room set at 37° C., and periodically checked for colour development.

Interpretation

The combination of colours that are produced as a result of the enzymatic breakdown of the substrates, and particularly the squares that they appear in, will allow the user to assess not only if the patient has a UTI, but the causative organism. Examples of how this is done have been shown below. Filters used were as follows: Filter 1=ME29, Filter 2=AVA, Filter 3=ME28

EXAMPLE 1

Results Following 4 Hours Incubation at 37° C.

|  | No filter | Filter 1 | Filter 2 | Filter 3 |
|---|---|---|---|---|
| Esculin | No colour | No colour | No colour | No colour |
| X-soln | N/A | Strong blue | Strong blue | Light blue |
| Mag-g | No colour | No colour | No colour | No colour |

From these results, we can confirm that the sample tested contained a microorganism as colour development occurred. As this colour development occurred with the X-gal and glc reagent, the causative organism was *E. coli*, which is able to pass though all three filters.

EXAMPLE 2

|  | No filter | Filter 1 | Filter 2 | Filter 3 |
|---|---|---|---|---|
| Esculin | Brown | Light Brown | No colour | No colour |
| X-soln | N/A | No colour | No colour | No colour |
| Mag-g | Purple/pink | Pink | No colour | No colour |

Again the patient is confirmed to have a UTI, however *E. coli* is not the causative organism as there is no colour development with the X-solution. Colour development has occurred with both esculin and mag-g. Three of our organisms will react with only Esculin and Mag-g, these are *E. faecalis, Pseudomonas* and *B. subtilis. Pseudomonas* and *B. subtilis* would be able to pass through filter 2 but there is no colour here, therefore these organisms are ruled out. only *B. subtilis* would be able to pass through filter 3, but there is no colour here, therefore *B. subtilis* is ruled out. Therefore the causative organism is *E. faecalis*, which can pass though filter 1.

EXAMPLE 3

|  | No filter | Filter 1 | Filter 2 | Filter 3 |
|---|---|---|---|---|
| Esculin | Brown | Brown | Brown | Light brown |
| X-soln | N/A | Dark blue | Dark blue | Blue |
| Mag-g | Pink | Pink | Pink | Light pink |

The majority of UTI's are caused by a single dominant organism, but in a few there maybe high levels of more than one. In some of these cases it may be possible to identify both of the organisms, as above, This sample would contain both *E. coli* and *B. subtilis*. Only *E. coli* will react with X-solution and pass though all three filters, only *B. subtilis* will react with both Esculin and Mag-g and pass though filter 3.

Device Embodiments

Embodiments of the present invention comprises layers of substrate, commencing with a backing card, followed by a wick and one or more colour development pads containing reagents to identify components, a sample application pad is presented on the top of the device. The devices may be encased in plastic or other suitable material and can have any number of windows, each corresponding with an area on the colour development pad below. This way, the device can be packaged, but the results not obscured by the packaging.

Preparing Membranes

Examples are all based on volumes of solutions required to soak a 5 cm×5 cm membrane, volumes can be adjusted in order to accommodate larger membranes.

EXAMPLE 1

Preparing an Esculin Membrane

A mixture of 0.1 g of esculin and 0.05 g of ferric ammonium citrate is dissolved in 100 ml distilled water. A solution of 0.1 M $MgCl_2$ is prepared by adding 2.033 g of $MgCl_2$ to 100 ml of distilled water. 2 ml of $MgCl_2$ is added to 10 ml of the esculin solution and mixed well. A 903 membrane is placed in a sterile container and the $MgCl_2$/Esculin solution poured over the membrane. The membrane is allowed to soak for 2-3 hours at room temperature. The membrane is then removed from the solution and placed in a container to dry at 37° C. in a well ventilated area. To allow even drying containers should be semi-closed. Drying may take up to 8 hours depending on conditions.

EXAMPLE 2

Preparing an X-gal+X-glc Membrane

Preparing X-gal Solution

A mixture of 0.04 g of 5-Bromo-4-Chloro-3-indoyl-beta-D-Galactopyranoside (X-gal) substrate is dissolved in 1 ml of 80% Dimethylformamide (DMF).

Preparing X-glc

A mixture of 0.02 g of 5-Bromo-4-Chloro-3-Indoxyl-beta-D-Glucuronide and cyclohexylammonium salt substrate is dissolved in 1 ml of 80% DMF.

Both X-gal and X-glc are added together to 100 ml of distilled water with 1 ml of 100 mM IPTG. The same soaking and drying procedure described in example 1 is applied.

EXAMPLE 3

Preparing Magenta—Glucoside Membrane

A mixture of 0.02 g Bromo-6-Chloro-3-Indolyl-β-D-Galactopyranoside (Mag-g) is dissolved in 80% DMF, and then added to 100 ml of distilled water. The same soaking and drying procedure described in example 1 is applied.

EXAMPLE 4

Preparing a Phosphate Buffered Membrane 1 g $NaH_2PO_4.2H2O$ and 1 g $Na_2HPO_4$ is added to 600 ml distilled water and the pH a to pH 7.8 using 1M solutions of these sodium salts.

A membrane is placed in a sterile container and 10 ml of the phosphate solution is poured over the 903 membrane and left to soak for 2-3 hrs at room temperature. The membrane is then removed from the solution and placed in a container to dry at 37° C. in a well ventilated area. To allow even drying containers should be semi-closed. Drying may take up to 8 hours depending on conditions.

Preparing Devices

Devices can be formulated into a number of different arrangements, suited to different testing environments.

Format 1

Layered Dipstick

The layered dipstick shown in FIG. 3 comprises a multi-layer arrangement of membranes and pore sized filters. The sample for testing is applied to the sample application pad at one end of the device, fluid is then drawn along the device to wick placed at the opposing end of the device. The sample for testing is first contacted with the uppermost membrane, fluid then passes though a first filtration membrane to remove the largest of organisms, and the sample is contacted with the next membrane containing a chromophore. The sample then meets a second filter which draws out intermediate sized organisms and is then contacted with the next membrane. The device is assembled onto a backing card.

Format 2

The Pyramid Device

Figure 5:
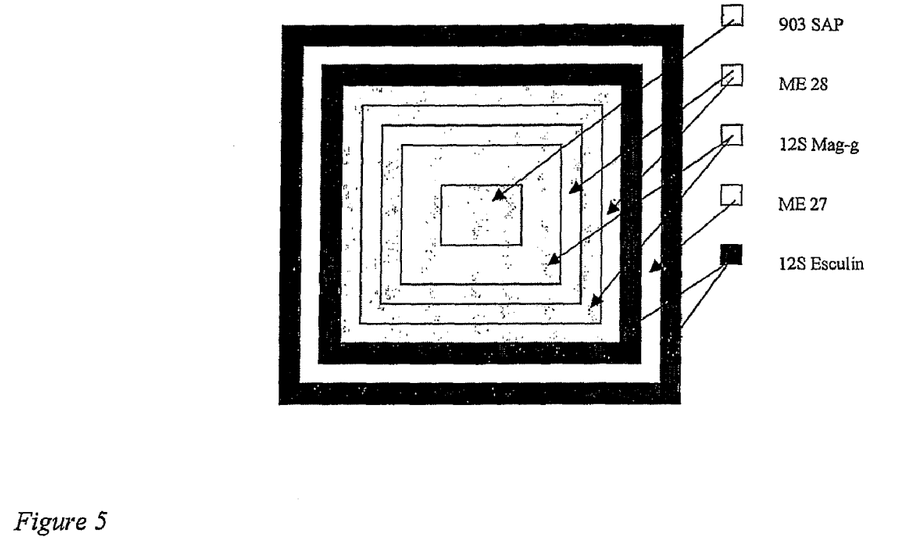
FIG. 5 shows a pyramid device in accordance with the invention

The pyramid device functions in much the same way as the layered dipstick device, but the layers are arranged in a different way. Membranes of progressively smaller size are applied one on top of another with filtration membranes between diagnostic membranes. A sample application pad is placed on the top of the stack. When a test is carried out the sample is applied to the sample application pad and is subsequently drawn downwards though the filters and membranes containing chromophores. Such an arrangement can be seen in FIG. 5. A casing having windows revealing appropriate diagnostic membranes can be placed around the pyramid.

Format 3

Panel Test Device

Figure 6A:
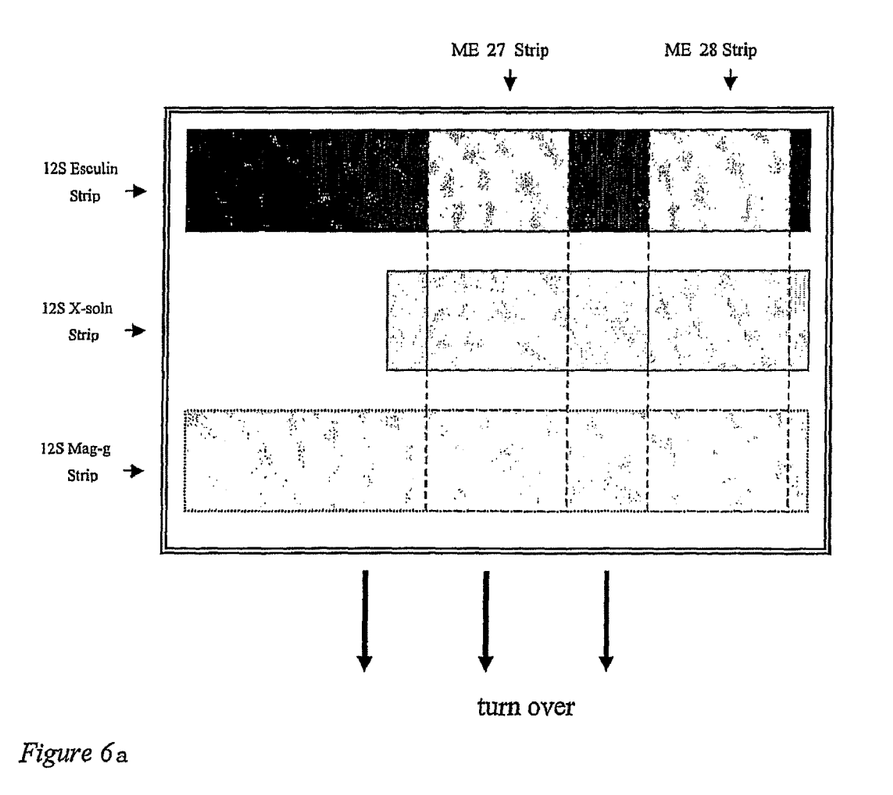
FIGS. 6a-c show a panel test device in accordance with the invention
Figure 6B:
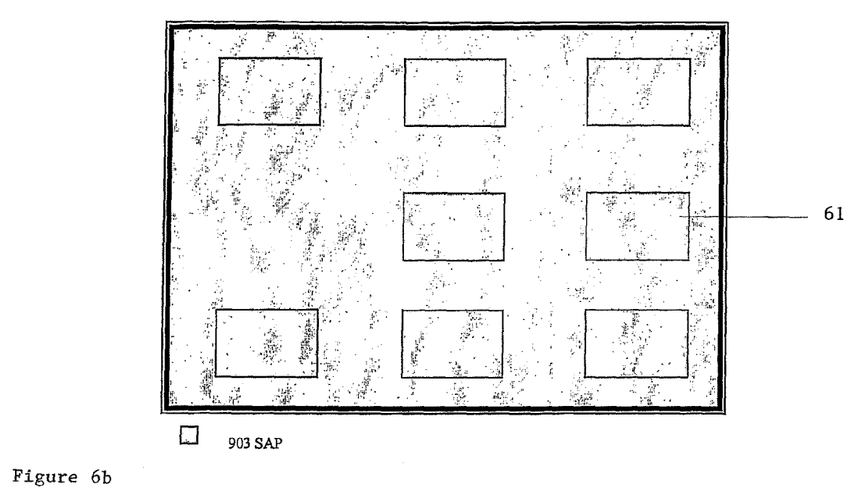
Figure 6C:
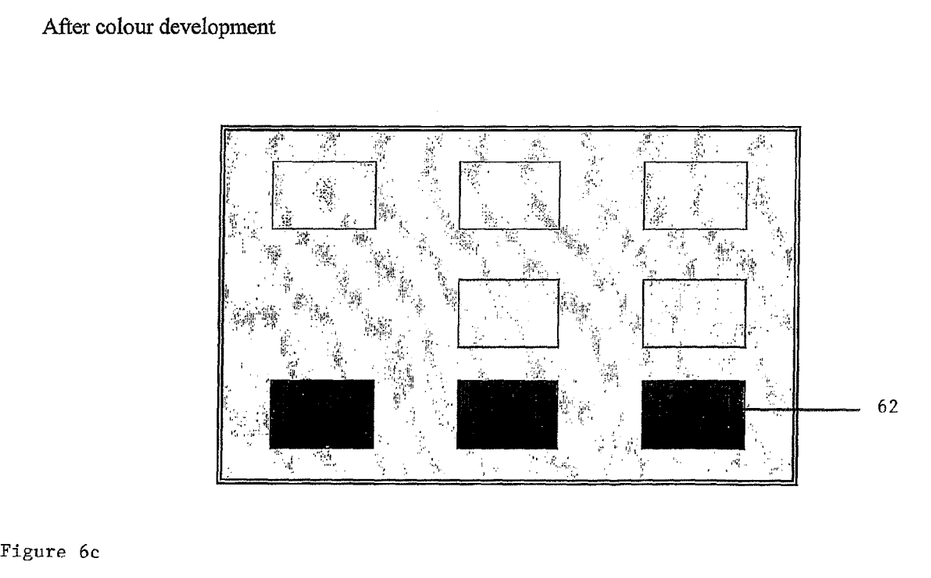

The panel test arrangement is shown in FIGS. 6a-c and comprises a number of rows and columns. Each row comprises a different substrate and each column, placed on over the row corresponds to a different filter. This arrangement allows different degrees of filtration to act on different areas of the same membrane, therefore identifying which organism is present. FIG. 6a shows an embodiment which the panel test is contained within a plastic casing having windows revealing sample application pads, solution to be tested is placed in each window and left to incubate. After incubation, to read the results the test is turned over (FIGS. 6b-c) and the potential colours that may develop, depending on infection, will be seen through transparent windows on the underside of the test. The type of infection present in the sample tested, will be determined through the absence (61) or presence of a colour (62) and the combination of colours seen. Test results can be cross referenced with a key printed onto the casing.

The diagnostic tests have been designed for use on hospital wards, in doctor's surgery's, pathology laboratories and in various outpatient departments with the possibility of direct patient use, perhaps in the home. Therefore simplicity in its use will be paramount in order to ensure that directions are followed and that the end results are interpreted correctly.

A sample of the patient's urine will be applied to the sample application pad either directly or indirectly. The test should then be placed in an incubator set at 37° C. to allow colour to develop, and periodically checked at intervals of ½ hr for no longer than 4 hrs. The results are viewed through windows 1-3, and compared against a chart to allow correct interpretation. The development of a colour/s, the combination of colours and time taken, will allow the reader to conclude if indeed the patient has a UTI, the bacteria involved.

Adaptation of Test for Different Organisms

The nature of UTI varies in different countries and continents. The test can be modified to detect different mixes of bacteria or individual bacteria which maybe more of a threat in a particular location or country.

*E. coli* Dipstick.

*E. coli* causes the majority of UTI cases reported, with figures varying between 50-85% depending on geographical location. Detection is specific as X-gal and X-glc only react with *E. coli* and therefore a dipstick dedicated solely to its detection would be useful in the field. In addition production costs of a less complex test would be driven down resulting in a cheap method of screening. Factors such as costs play a critical role in the level of healthcare available and are therefore important.

*Pseudomonas* Dipstick.

There has been a reported increase in non-EU countries in resistance rates of *P. aeroginosa* to certain antibiotics. This is largely due to oversubscribing of antibiotics to patients without determining the exact cause of the infection. Therefore by providing a means of detection through the use of a simple, cheap and rapid test would allow more effective screening of patients during the first stages of assessment, and hence correct treatment.

Different combination of reagents and membranes can be provided to test for different bacteria. Devices can be manufactured for use in technical laboratories, where the need for casing and indicator cards may not be required. For the public market, plastic casing with windows and a results interpretation card can be provided. One embodiment is envisaged where a colour key is provided on the casing adjacent each window, detailing the results corresponding to each possible colour.

The invention claimed is:

1. A device for detecting and identifying a plurality of different microorganisms present in a single sample comprising a porous body having a plurality of regions of differing pore sizes, each of the said plurality of regions being associated with a plurality of different chromogens specific to enzymes produced by microorganisms.

2. The device of claim 1 wherein the porous body comprises membranes impregnated with chromogens.

3. The device of claim 1 in which the porous body comprises a plurality of membranes having differing pore sizes.

4. The device of claim 3 wherein the pore sizes vary from 0.6 μm to 3.5 μm.

5. The device of claim 2 wherein the membranes are cellulose membranes.

6. The device of claim 2 in which the chromogens are specific to different enzymes.

7. The device of claim 2 in which the chromogens impart a characteristic color to different bacterial colonies.

8. The device of claim 2 wherein the chromogens comprise a chromogenic substrate selected from the group consisting of Indoxyl butyrate, Indoxyl glucoside, Esculin, Magenta glucoside, Red-β-glucuronide, 2-methoxy-4-(2-nitrovinyl) phenyl β-D-glucopyranoside (MNP-glc), 2-methoxy-4-(2-nitrovinyl) phenyl β-D-2acetamido-2-deoxyglucopyranoside (MNP-glcNAc), 5-Bromo-4-Chloro-3-Indoxyl-beta-D-Glucuronide, Cyclohexylammonium Salt (X-Glc), and 5-Bromo-4-Chloro-3-indoyl-beta-D-Galactopyranoside (X-gal).

9. The device of claim 1 wherein the porous body further comprises a phosphate buffer.

10. The device of claim 1 wherein the porous body further comprises Isopropyl-β-D-thiogalactopyranoside.

11. The device of claim 1 wherein the porous body further comprises $Mg^{2+}$ ions.

12. The device of claim 2 wherein the membranes are presented in a layered arrangement, with an uppermost layer comprising a sample application pad of a rapid adsorption pad impregnated with a phosphate buffer, subsequent regions are in the form of layers having pore sizes of 3.0 µm, 1.2 µm, 0.8 µm and 0.6 µm, respectively.

13. The device of claim 2 wherein the membranes are presented in row and column arrangements, each row comprising a particular substrate and each column comprising a different membrane with a different corresponding pore size.

14. A method for detecting and identifying bacteria using a device comprising a porous body having a plurality of regions of differing pore size, said regions being associated with a plurality of different chromogens specific to enzymes produced by microorganisms, wherein the method comprises the steps of:
 a) applying a solution containing bacteria to the porous body at a region having a largest pore size,
 b) allowing the solution to wick through the porous body,
 c) allowing the device to develop in an incubator set to a temperature of about 37° C., and
assessing the colors developed on the device in order to identify the bacteria present.

15. The method of claim 14, wherein the porous body comprises membranes impregnated with chromogens.

16. The method of claim 14, wherein the porous body comprises a plurality of membranes having differing pore sizes.

17. The method of claim 16, wherein the pore sizes vary from 0.6 µm to 3.5 µm.

18. The method of claim 15, wherein the membranes are cellulose membranes.

19. The method of claim 15, wherein the chromogens are specific to different enzymes.

20. The method of claim 15, wherein the chromogens impart a characteristic color to different bacterial colonies.

* * * * *